United States Patent [19]

Rosinger et al.

[11] 4,085,147

[45] Apr. 18, 1978

[54] PREPARATION OF META-ARYLOXY-BENZALDEHYDES

[75] Inventors: Herbert P. Rosinger; Derek A. Wood, both of Sittingbourne, England; Roger A. Sheldon, Amsterdam, Netherlands

[73] Assignee: Shell Oil Company, Houston, Tex.

[21] Appl. No.: 762,541

[22] Filed: Jan. 26, 1977

[30] Foreign Application Priority Data

Feb. 5, 1976 United Kingdom ................ 4577/76
Jul. 2, 1976 United Kingdom ............... 27675/76

[51] Int. Cl.$^2$ ............................................. C07C 45/00
[52] U.S. Cl. ........................... 260/600 R; 260/612 R; 204/163 R; 260/512 C
[58] Field of Search ............................ 260/600 R, 599

[56] References Cited

U.S. PATENT DOCUMENTS

| | | | |
|---|---|---|---|
| 2,816,144 | 12/1957 | Harris | 260/599 |
| 3,499,934 | 3/1970 | Pyne | 260/599 |
| 3,524,885 | 8/1970 | Deinet | 260/599 |
| 3,700,736 | 10/1972 | Yomamoto et al. | 260/599 X |

OTHER PUBLICATIONS

Organic Reactions, vol. 8, (1954), pp. 197–209.
Angyal et al., Jour. Chem Soc., (1949), pp. 2700–2704.
Kirk–Othmer, Encyclopedia of Chem. Tech., 2nd Ed., vol. 3, (1964), p. 362.

*Primary Examiner*—Bernard Helfin

[57] ABSTRACT

Meta-aryloxybenzaldehydes are prepared by treating a mixture of meta-aryloxybenzyl- and benzal halides with hexamethylenetetramine (or equivalent amounts of ammonia and formaldehyde) and hydrolyzing the resulting product under acid conditions.

12 Claims, No Drawings

PREPARATION OF META-ARYLOXY-BENZALDEHYDES

BACKGROUND TO THE INVENTION

This invention relates to an improved process for the preparation of meta-aryloxy-benzaldehydes, these compounds being valuable intermediates, for example, in the preparation of pesticides containing a meta-aryloxy-benzyl group. Such pesticides include meta-aryloxy-benzyl esters of substituted cyclopropane-carboxylic acid and chlorophenyl-acetic acids which have outstanding insecticidal properties.

A possible route to the preparation of a meta-aryloxy-benzaldehyde is by the halogenation of the corresponding meta-aryloxy-toluene to form the benzyl halide, followed by conversion of that halide into the benzaldehyde. However, although this route is satisfactory in principle, it does suffer from certain drawbacks, namely (i) the need to control the conditions of the halogenation step to provide the maximum yield of benzyl halide at the expense of the overall yield of other halogenated products (e.g., benzal halide and ring-halogenated products) and (ii) the yield of benzyl halide rarely exceeds 70%.

It has now been found that these drawbacks can be minimized by the adoption of a modified process which enables mixtures of side-chain halogenated meta-aryloxy-toluenes, especially a mixture of the benzyl and benzal halides to be converted into the aldehyde.

DESCRIPTION OF THE INVENTION

The present invention provides a process for the preparation of meta-aryloxy-benzaldehydes, which comprises in a first step reacting a mixture of the corresponding meta-aryloxy-benzyl and -benzal halides with ammonia and formaldehyde and, in a second step, hydrolyzing the resulting product under acid conditions to form the meta-aryloxy-benzaldehyde.

Instead of ammonia and formaldehyde, hexamethylenetetramine may be employed in the first step of the process according to the invention and it will be appreciated that the use of hexamethylene tetramine produces a similar result because of the chemical equilibrium existing between the latter compound and ammonia and formaldehyde. Thus, ammonia and formaldehyde may be regarded as precursors to hexamethylenetetramine or the latter may be regarded as a generator of ammonia and formaldehyde.

Although aqueous conditions are not essential to the first step in the process according to the invention and reaction in a non-aqueous solvent such as chloroform can be effected, aqueous conditions may be conveniently employed in anticipation of the hydrolysis reaction in the second step of the process. Aqueous ammonia, formalin or aqueous hexamethylene tetramine may therefore be used. The first step of the process is an exothermic reaction and, generally, no heat is required to initiate reaction; reaction temperatures in the range of from 10° to 150° C may conveniently be used in practice.

The product of the first step of the process according to the invention is a mixture comprising a benzyl halide complex salt and substantially unchanged benzal halide; both these products may be isolated and then subjected to a hydrolysis procedure but it has been found that this is unnecessary and hydrolysis of the reaction mixture from the first step proceeds smoothly and efficiently.

The hydrolysis is preferably carried out at a pH in the range of from 3 to 6.5, better results being obtained at a pH in the range of from 5 to 6. The acid used to achieve these pH values may be organic or inorganic and suitable examples are acetic acid, phosphoric acid, hydrochloric acid or sulphuric acid; acetic acid has proved to be very useful in this respect, especially 50% by weight acetic acid. Hydrolysis may be achieved by refluxing the acidified reaction mixture or by any other convenient means; temperatures in the range from 80° to 200° C are generally suitable, temperatures in the range of from 80° to 120° C being preferable.

It has been found that the first step of the process according to the invention may be carried out in the presence of the acid employed in the hydrolysis step and that better yields are achieved by this means. For example, the first step may be carried out by adding the benzyl and benzal halides to a solution of hexamethylene tetramine dissolved in acetic acid and refluxing the resulting mixture.

It has also been found that the hydrolysis reaction may be facilitated by the presence of a mineral acid, for example hydrochloric acid, and this may be added in the first or second step of the process according to the invention or, if desired, towards the end of the hydrolysis reaction.

One considerable advantage of the process according to the invention is that it will accept mixtures of the benzyl and benzal halides in any proportion. As existing economic routes to the benzyl halide result in the co-production of some dihalide, i.e., some benzal halide, the present process enables these mixtures to be converted into the corresponding benzaldehyde without the need to separate out and remove the dihalide. It is remarkable that the dihalide is not affected to any appreciable extent during the reaction in the first step of the process according to the invention and that it together with the benzyl halide complex is hydrolyzed to form the desired aldehyde in the second step.

Excellent results in terms of aldehyde yield have been obtained with mixtures of the benzyl and benzal bromides and the benzyl and benzal chlorides.

The mixture of benzyl and benzal halides can be obtained by any convenient means but it has been found that such a mixture can be readily prepared by a halogenation reaction on the appropriate toluene. According to an aspect of the present invention, therefore, the mixture of meta-aryloxy-benzyl halide and -benzal halide used as starting material in the process according to the invention can be prepared by a process which comprises halogenating the corresponding meta-aryloxy-toluene with gaseous halogen at an elevated temperature in the presence of a free radical initiator. The temperature of the halogenation reaction depends very largely on the nature of the halogen employed and the need to avoid ring halogenation of the toluene. A general temperature range for the halogenation reaction is of from 50° to 250° C.

So far as bromination is concerned it has been found that better results are obtained by contacting the meta-aryloxy-toluene with gaseous bromine at a temperature in the range of from 180°–250° C, preferably in the presence of ultra-violet light as the free radical initiator. For maximum overall yields of the benzyl and benzal bromides, a molar excess of the gaseous bromine is preferably used, e.g., at least 10% and generally at least 25% based on the molar quantity of the starting toluene; a molar excess in the range of from 10 to 30% can generally be employed. The use of such excess bromine inevitably results in the formation of a larger proportion of the benzal bromide than when a stoichiometric amount or a slight molar deficiency of bromine is used. However, since the process according to the invention can readily convert both mono- and di-bromides into the corresponding aldehyde, the presence of a larger proportion of dibromide in the resulting brominated mixture presents no problems. Overall yields of benzyl and benzal bromides of over 90% can be achieved by this route.

So far as chlorination of the meta-aryloxy-toluene is concerned it has been found that better results are obtained by contacting the meta-aryloxy-toluene in a non-polar solvent at a temperature in the range of from 40–100° C with gaseous chlorine, the free radical initiator preferably being a peroxide or azo-initiator, such as benzoyl peroxide or azo-isobutyronitrile (AIBN). The non-polar solvent selected for this chlorination reaction must be such that it does not promote the formation of ring-chlorinated products and is itself substantially unaffected by the prevailing chlorination conditions. Generally speaking, halogenated hydrocarbons are satisfactory solvents for this reaction, for example, carbon tetrachloride and chlorobenzene; excellent results have been obtained with carbon tetrachloride as the solvent. In order to favour the side-chain chlorination of the toluene and suppress ring chlorination it has been found desirable to prevent the chlorination of the toluene occurring at high concentrations, for example over 60% by weight of toluene in solvent; concentrations in the range of from 5 to 50% by weight have been found to be generally preferable. Further, the conversion of the toluene should not be allowed to proceed to completion because this tends to produce unwanted chlorinated products; thus the reaction should be stopped at a conversion in the range of from 95–99% based on meta-aryloxy-toluene, suitably 98 or 99%. As with the bromination reaction overall yields of the mono- and dichloride are generally over 90% and often over 95%.

The nature of the meta-aryloxy substituent in the starting material and in the product according to the invention is unimportant but the commercially-useful product in terms of its importance to the synthesis of synthetic pesticidal pyrethroids is the meta-phenoxy-benzaldehyde.

It will be appreciated, therefore, that the present invention provides a valuable route to meta-phenoxy-benzaldehyde starting from meta-phenoxy-toluene without the need to isolate a particular intermediate chloride or bromide for conversion into the aldehyde. An important attribute of the process is its flexibility in being able to convert a mixture in any proportions of meta-phenoxy-benzyl halide and meta-phenoxy-benzal halide (i.e., a mixture of the mono- and di-halides) to the desired aldehyde.

Accordingly, a particular aspect of the invention concerns a process for the preparation of meta-phenoxy-benzaldehyde which comprises:

(a) preparing a mixture of meta-phenoxy-benzyl halide and meta-phenoxy-benzal halide by halogenating meta-phenoxy-toluene with gaseous halogen at an elevated temperature in the presence of a free radical initiator;

(b) reacting the mixture of halides prepared in (a) with ammonia and formaldehyde, or hexamethylene tetramine; and (c) hydrolyzing the reaction product from (b) under acid conditions to form the meta-phenoxy-benzaldehyde.

The process according to the invention is further illustrated in the following Examples:

EXAMPLE I

(a) Preparation of meta-phenoxy-benzyl and -benzal bromide

3-Phenoxytoluene (430 g; 2.337 mol.) was treated with a stream of bromine (473 g; 2.956 mol.) under a nitrogen atmosphere in a 5-liter vessel containing a source of ultraviolet light and designed so that bromine is introduced close to the U.V.-source and the Reactants vigorously circulated. The bromine was thus present in a 26.5% mol. excess over the phenoxy-toluene. When addition was complete (about 3 hours) the reaction mixture was allowed to cool overnight whilst being flushed with a stream of nitrogen. This yielded 627 g of bromination product having the following composition:

3-phenoxy toluene (unconverted):2.1%
3-phenoxy benzyl bromide:61.5%
3-phenoxy benzal bromide:36.4%

(b) Preparation of meta-phenoxy-benzaldehyde

The bromination mixture resulting from (a) above was added to 1 liter glacial acetic acid and 350 g hexamethylene tetramine (2.5 mol.), followed by 1 liter water. After maintaining under reflux (105° C) for 4 hours, 500 ml of concentrated hydrochloric acid were added followed 5 minutes later by 700 ml of water, and the mixture refluxed for a further 15 minutes.

After cooling to room temperature by immersion in ice water, the reaction mixture was extracted with methylene dichloride (3 × 500 ml). The combined extracts were washed neutral (pH 7–8) with saturated sodium bicarbonate, and then washed once with 1 liter water 10% ice-cold hydrochloric acid and once with 1 liter water. After drying over anhydrous sodium sulphate the methylene dichloride was distilled off and the residual product degassed to constant weight under high vacuum (0.1 mm Hg) to yield 430.5 g (2.172 mol.) of 3-phenoxy-benzaldehyde.

N.M.R. analysis of this product established its purity as 95%, and G.L.C. analysis showed that all the benzyl bromide and benzal bromide had reacted. The yield of 3-phenoxybenzaldehyde (2.172 mol.) was 93% based on the starting 3-phenoxytoluene (2.337 mol.).

EXAMPLE II

Preparation of meta-phenoxy-benzaldehyde from the corresponding benzyl and benzal bromides Brominated m-phenoxytoluene (33.65 g), as obtained in Example I(a), was added to a solution of hexamethylene tetramine (16.8 g) dissolved in chloroform (140 ml). The mixture was stirred overnight and then filtered to give the salt (41.5 g) which was dissolved in acetic acid (35 ml) and water (35 ml) and was heated under reflux for 4 hours. After the addition of concentrated hydrochloric acid (27 ml), reflux was continued for a further 0.5 hour. The cooled reaction mixture was extracted with methylene chloride (3 × 20 ml), the organic extract washed neutral with aqueous sodium bicarbonate solution and then the solvent was evaporated and the residue distilled to give m-phenoxybenzaldehyde (14.6 g; 61%) as a colourless liquid, b.p. 140°-141° C/1 mm Hg.

EXAMPLE III

Preparation of meta-phenoxy-benzaldehyde from the corresponding benzyl and benzal chlorides A mixture of 3-phenoxybenzyl chloride and 3-phenoxy-benzal chloride (50 g), containing 60% monochloride and 40% dichloride, was added to a solution of hexamethylenetetramine (35 g) dissolved in acetic acid (100 ml). Water (100 ml) was added and the mixture heated under reflux for 4 hours. Concentrated hydrochloric acid was then added and the mixture refluxed for a further 15 minutes.

After cooling to room temperature the reaction mixture was extracted with methylene chloride (3 × 50 ml). The combined extracts were washed neutral with aqueous sodium bicarbonate solution, dried over anhydrous sodium sulphate, and then evaporated to give 3-phenoxybenzaldehyde (41.9 g, yield 97%).

EXAMPLE IV

Preparation of meta-phenoxy-benzaldehyde from the corresponding benzyl and benzal bromides A solution of formalin (40%, 50 ml) was cooled to 10° C and then treated with aqueous ammonia solution (35%, 25 ml) over 15 minutes. Crude bromide mixture (25 g), as obtained in Example I(a), was added and the mixture stirred under a nitrogen blanket for 4 hours. The mixture was then acidified with acetic acid (50 ml) and heated under reflux for 3 hours. After cooling, the reaction mixture was extracted with toluene (25 ml) and the extract washed neutral with sodium bicarbonate solution. The toluene solution of crude 3-phenoxybenzaldehyde was diluted with an equal quantity of ethanol and then stirred with a saturated aqueous solution of sodium bisulphite. The resulting bi-sulphite compound was filtered off and washed with toluene until free from coloured impurities. After vacuum drying, this gave 20.5 g of purified 3-phenoxybenzaldehyde bi-sulphite compound which on treatment with dilute mineral acid yielded the pure 3-phenoxybenzaldehyde. Yield based on chloride mixture was 77%.

EXAMPLES V–VII

Preparation of a mixture of meta-phenoxybenzyl chloride and meta-phenoxybenzal chloride Chlorine was bubbled into a refluxing solution (80° C) of meta-phenoxy-toluene (10 g) and initiator (0.25 g) in carbon tetrachloride (100 ml) as solvent. A series of runs were performed with different reaction times and different initiators, and the results are shown in the following Table I.

From these results it will be seen that the selectivity (i.e., the sum of the % weight of mono- and dichloride) depends on the presence of a free radical initiator and on preventing the complete conversion of the toluene (see Example VI where the selectivity is relatively poor when the reaction is allowed to proceed to complete conversion).

In another series of experiments it was shown that the selectivity also depends on the toluene concentration in the solvent, namely that selectivity decreases with increasing toluene concentrations.

| Example | Initiator | Reaction time (hr) | Conversion of toluene (%) | Product Composition (%wt) | | | Selectivity (%) (Mono- + di-chloride) |
|---|---|---|---|---|---|---|---|
| | | | | Mono-chloride | Di-chloride | Im-purities** | |
| V* | AIBN | 0.75 | 77 | 84.5 | 14.9 | 0.6 | 99.4 |
| | | 1.00 | 93 | 74.5 | 24.2 | 1.3 | 98.7 |
| | | 1.50 | 99 | 54.9 | 42.0 | 3.1 | 96.9 |
| VI* | AIBN | 3.00 | 100 | 2.7 | 66.3 | 30.9 | 69.0 |
| VII | BP | 1.00 | 98 | 67.3 | 32.1 | 0.6 | 99.4 |
| Control | None | 1.00 | 14 | 61.0 | 11.0 | 28.0 | 72.0 |
| | | 3.00 | 27 | 65.0 | 8.5 | 26.5 | 73.5 |
| | | 7.00 | 47 | 64.0 | 9.4 | 26.6 | 73.4 |

*with nitrogen purge;
AIBN - azoisobutyronitrile;
BP - benzoyl peroxide
**nuclear-chlorinated products

EXAMPLE VIII

Preparation of meta-phenoxy-benzaldehyde from the corresponding benzyl and benzal chlorides A solution of formalin (40%, 150 ml) was cooled to 10° C and then treated with aqueous ammonia solution (35%, 75 ml) over 15 minutes. A mixture of 3-phenoxybenzyl chloride and 3-phenoxybenzal chloride containing 70% monochloride chloride and 30% dichloride mixture (50 g) was added and the mixture stirred under a nitrogen blanket for 3 hours. The mixture was then acidified with acetic acid (150 ml), stirred for a further 3 hours in the cold, and then refluxed for 4 hours. After cooling, the reaction mixture was extracted with toluene (100 ml) and the extract washed neutral with sodium bicarbonate solution. The toluene solution of crude 3-phenoxybenzaldehyde was diluted with an equal quantity of ethanol and then stirred with a saturated aqueous solution of sodium bisulphite. The resulting bisulphite adduct was filtered off and washed with toluene. After vacuum drying, this gave 63.0 g of purified 3-phenoxybenzaldehyde bisulphite compound which on treatment with dilute mineral acid yielded the pure 3-phenoxybenzaldehyde. Yield based on chloride mixture was 95%.

We claim:
1. A process for preparing meta-phenoxybenzaldehyde, which comprises bringing together
   (a) hexamethylenetetramine and
   (b) a mixture of a meta-phenoxybenzyl halide and a meta-phenoxybenzal halide, wherein the halogen is bromine or chlorine, and treating the resulting product with an aqueous solution of acetic acid, said solution having a pH in the range of 5 to 6, at a temperature in the range of 80° C to 120° C.
2. A process according to claim 1 wherein the hydrolysis is affected in situ by bringing the reagents (a) and

(b) together in the presence of the aqueous acid at the indicated temperature.

3. A process according to claim 1 wherein the hexamethylenetetramine is replaced by equivalent amounts of ammonia and formaldehyde.

4. A process according to claim 3 wherein the hydrolysis is effected in situ by bringing the reagents (a) and (b) together in the presence of the aqueous acid at the indicated temperature.

5. A process according to claim 1 wherein the halogen is bromine.

6. A process according to claim 2, wherein the halogen is bromine.

7. A process according to claim 3, wherein the halogen is bromine.

8. A process according to claim 4, wherein the halogen is bromine.

9. A method for preparing meta-phenoxybenzaldehyde, which comprises adding a mixture of a meta-phenoxybenzyl halide and a meta-phenoxybenzal halide, wherein the halogen is bromine or chlorine, to a solution of hexamethylenetetramine in aqueous acetic acid, the solution having a pH in the range of 5 to 6, and the resulting admixture.

10. A process according to claim 9 wherein the hexamethylenetetramine is replaced by equivalent amounts of ammonia and formaldehyde.

11. A process according to claim 10, wherein the halogen is bromine.

12. A process according to claim 9, wherein the halogen is bromine.

* * * * *

UNITED STATES PATENT AND TRADEMARK OFFICE
CERTIFICATE OF CORRECTION

PATENT NO. : 4,085,147
DATED : April 18, 1978
INVENTOR(S) : HERBERT P. ROSINGER, DEREK A. WOOD and ROGER A. SHELDON It is certified that error appears in the above–identified patent and that said Letters Patent are hereby corrected as shown below:

Claim 9, at the beginning of the last line, insert "refluxing".

Signed and Sealed this

Twenty-second Day of August 1978

[SEAL]

Attest:

RUTH C. MASON
Attesting Officer

DONALD W. BANNER
Commissioner of Patents and Trademarks